(12) United States Patent
Hawwa et al.

(10) Patent No.: US 7,597,003 B2
(45) Date of Patent: Oct. 6, 2009

(54) ACOUSTIC CHAMBER FOR DETECTION OF INSECTS

(75) Inventors: Muhammad A. Hawwa, Dhahran (SA); Faleh A. Al-Sulaiman, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 322 days.

(21) Appl. No.: 11/822,384

(22) Filed: Jul. 5, 2007

(65) Prior Publication Data

US 2009/0007670 A1    Jan. 8, 2009

(51) Int. Cl.
G01N 29/14    (2006.01)
G01N 29/22    (2006.01)

(52) U.S. Cl. .......................................... 73/571; 73/587

(58) Field of Classification Search ............... 73/571, 73/587
See application file for complete search history.

(56) References Cited

U.S. PATENT DOCUMENTS

| | | | | |
|---|---|---|---|---|
| 1,863,672 | A * | 6/1932 | Repp | 43/108 |
| 2,030,052 | A * | 2/1936 | Bernitz, Sr. | 47/32.5 |
| 4,671,114 | A | 6/1987 | Litzkow et al. | |
| 4,809,554 | A * | 3/1989 | Shade et al. | 73/587 |
| 4,937,555 | A | 6/1990 | Litzkow et al. | |
| 4,941,356 | A | 7/1990 | Pallaske | |
| 4,991,439 | A | 2/1991 | Betts | |
| 5,005,416 | A | 4/1991 | Vick et al. | |
| 5,285,688 | A | 2/1994 | Robbins et al. | |
| 5,473,942 | A | 12/1995 | Vick et al. | |
| 5,616,845 | A | 4/1997 | Hickling et al. | |
| 5,877,422 | A | 3/1999 | Otomo | |
| 6,052,066 | A | 4/2000 | Su | |
| 6,230,435 | B1 * | 5/2001 | Carman | 43/108 |
| 6,347,551 | B1 * | 2/2002 | Turpening et al. | 73/628 |
| 6,801,131 | B2 | 10/2004 | Donskoy et al. | |
| 6,813,948 | B1 * | 11/2004 | Rinn | 73/584 |
| 6,883,375 | B2 | 4/2005 | Dunegan | |
| 6,923,064 | B2 | 8/2005 | Rodriguez Gobernado et al. | |
| 2005/0199065 | A1 | 9/2005 | Dunegan | |
| 2006/0028345 | A1 | 2/2006 | Lee | |
| 2007/0066897 | A1 * | 3/2007 | Sekins et al. | 600/437 |
| 2007/0194658 | A1 * | 8/2007 | Zhang et al. | 310/314 |

FOREIGN PATENT DOCUMENTS

GB    1407357    9/1975

* cited by examiner

*Primary Examiner*—Hezron Williams
*Assistant Examiner*—Rose M Miller
(74) *Attorney, Agent, or Firm*—Richard C. Litman

(57) ABSTRACT

The acoustic chamber for the detection of insects provides for the acoustic detection of insects living within the trunk of a tree. The chamber includes an annular shell disposed around the trunk of the tree to define an annular acoustic or sound chamber. Acoustic sensors are mounted in the shell walls. The acoustic sensors may be microphones that extend from the shell to be in direct contact with the tree trunk, or microphones spaced apart from the tree trunk, or other suitable acoustic transducers. The acoustic sensors are connected to data processing equipment for analyzing sounds picked up by the sensors for acoustic signals indicative of insect infestation.

20 Claims, 6 Drawing Sheets

ACOUSTIC CHAMBER FOR DETECTION OF INSECTS

BACKGROUND OF THE INVENTION

1. Field of the Invention

The present invention relates to devices for the early detection of insect infestation of trees, and particularly to an acoustic chamber for detection of insects that provides an acoustic chamber around the trunk of a tree, the chamber being equipped with acoustic sensors and monitoring equipment for the detection of insect infestation.

2. Description of the Related Art

Insects, such as red palm weevils (*Rhynchophorus ferrugineus*), are the cause of considerable destruction of natural resources, primarily through infestation of trees and plants. When red palm weevils initially infest a tree, the insects dig tunnels into the tree trunk, burrowing into the soft, central portion of the trunk. Once the central portion of the trunk is reached, the insects and their larvae begin ingesting the trunk from the inside, eventually leaving a mostly hollow tree trunk, thus killing the tree.

Such infestation is generally not noted from visual inspection alone until the tree is already dead or close to dying. Thus, it is necessary to be able to detect the infestation of the wood during the initial tunneling stage of the insects.

Laboratory acoustic tests have shown that insects' activities within the wood can be monitored through detection of acoustic signals generated by the insects. Various steps in the infestation process, such as eating, moving, spinning and digestion have been monitored and have each been found to generate a unique acoustic signal or signature, which may be monitored and analyzed. In a large-scale agricultural environment, such as a tree farm, the ambient noise unfortunately makes the detection and analysis of such signals extremely difficult. There is a need for a device that can be used for acoustic monitoring of insect activity in environmental settings that provides a signal-to-noise ratio comparable to that which can be obtained in the laboratory in order to provide for early detection of insect infestation in trees, particularly in commercially valuable trees.

Thus, an acoustic chamber for detection of insects solving the aforementioned problems is desired.

SUMMARY OF THE INVENTION

The acoustic chamber for the detection of insects provides for the acoustic detection of insects living within the trunk of a tree. The chamber includes an annular shell disposed around the trunk of the tree to define an annular acoustic or sound chamber. Acoustic sensors are mounted in the shell walls. The acoustic sensors may be microphones that extend from the shell to be in direct contact with the tree trunk, or microphones spaced apart from the tree trunk, or other suitable acoustic transducers. The acoustic sensors are connected to data processing equipment for analyzing sounds picked up by the sensors for acoustic signals indicative of insect infestation.

The wall(s) of the annular shell may be made from material that reflects sounds waves to insulate the acoustic sensors from environmental noise external to the shell, and to enhance pickup of sounds emanating from the trunk of the tree. The annular shell may have an annular base having a U-shaped groove defined in its upper surface for supporting the shell wall(s), and a layer of spongy, resilient, sound-absorbing material lining the inner surface of the base element, the sound-absorbing material being covered by a sound-reflecting material facing the acoustic chamber, the sound-absorbing material insulating the acoustic chamber from noise entering from ground level. Similarly, the annular shell may have a top peripheral rim lined with a spongy, resilient sound-absorbing material having a layer of sound-reflecting material facing the acoustic chamber, the sound-absorbing material insulating the acoustic chamber from environmental noise entering at the top of the shell.

The annular shell may have a cylindrical wall made from arcuate segments, with adjoining segments being joined by tongue and groove joints. Alternatively, the annular shell may be polygonal in transverse cross section, having a plurality of flat wall panels joined by elongated connectors forming the angles of the polygon and having grooves along both edges to snap in the edges of the panels.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
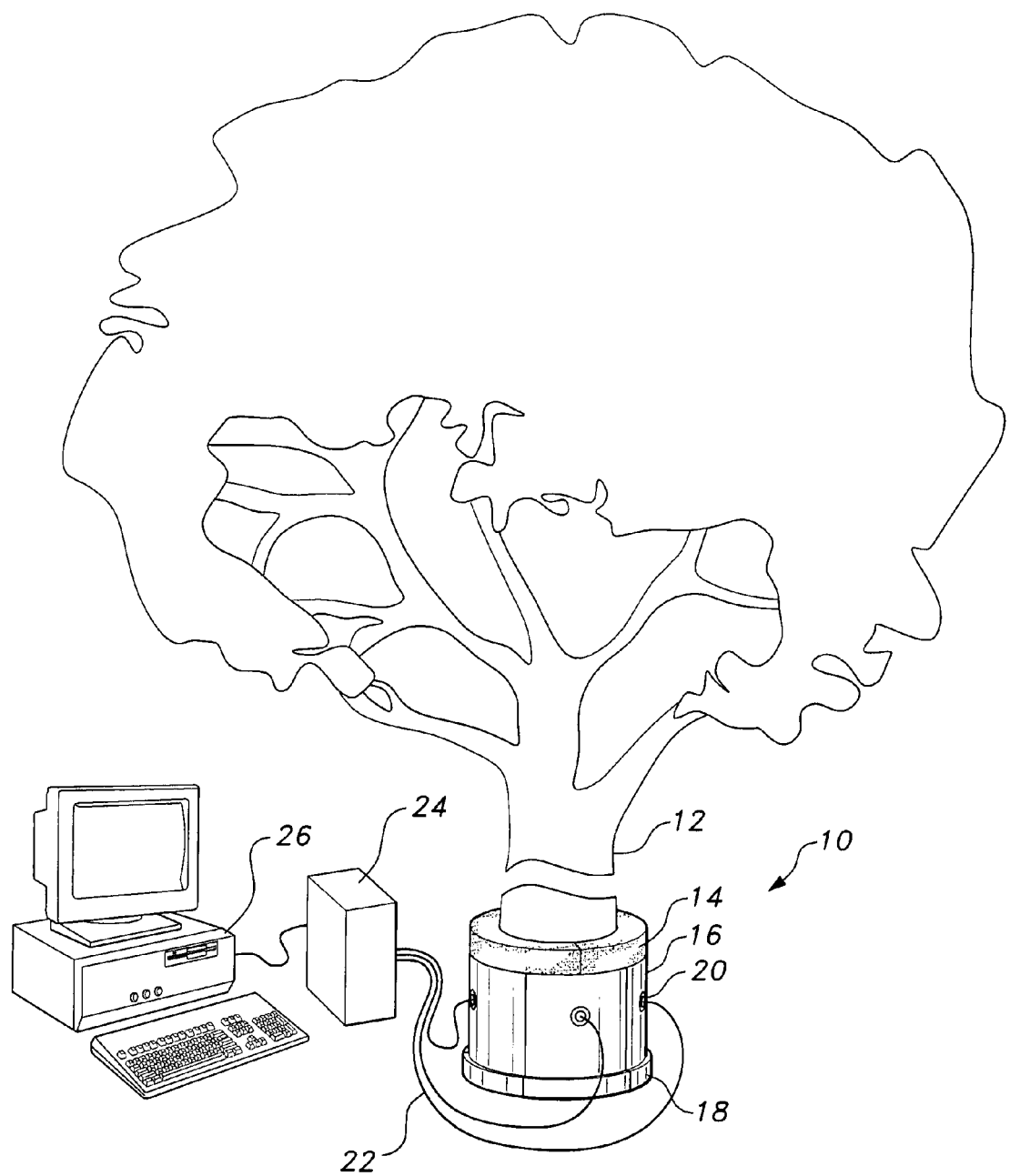
FIG. 1 is an environmental, perspective view of an acoustic chamber for detection of insects according to the present invention.
Figure 5:
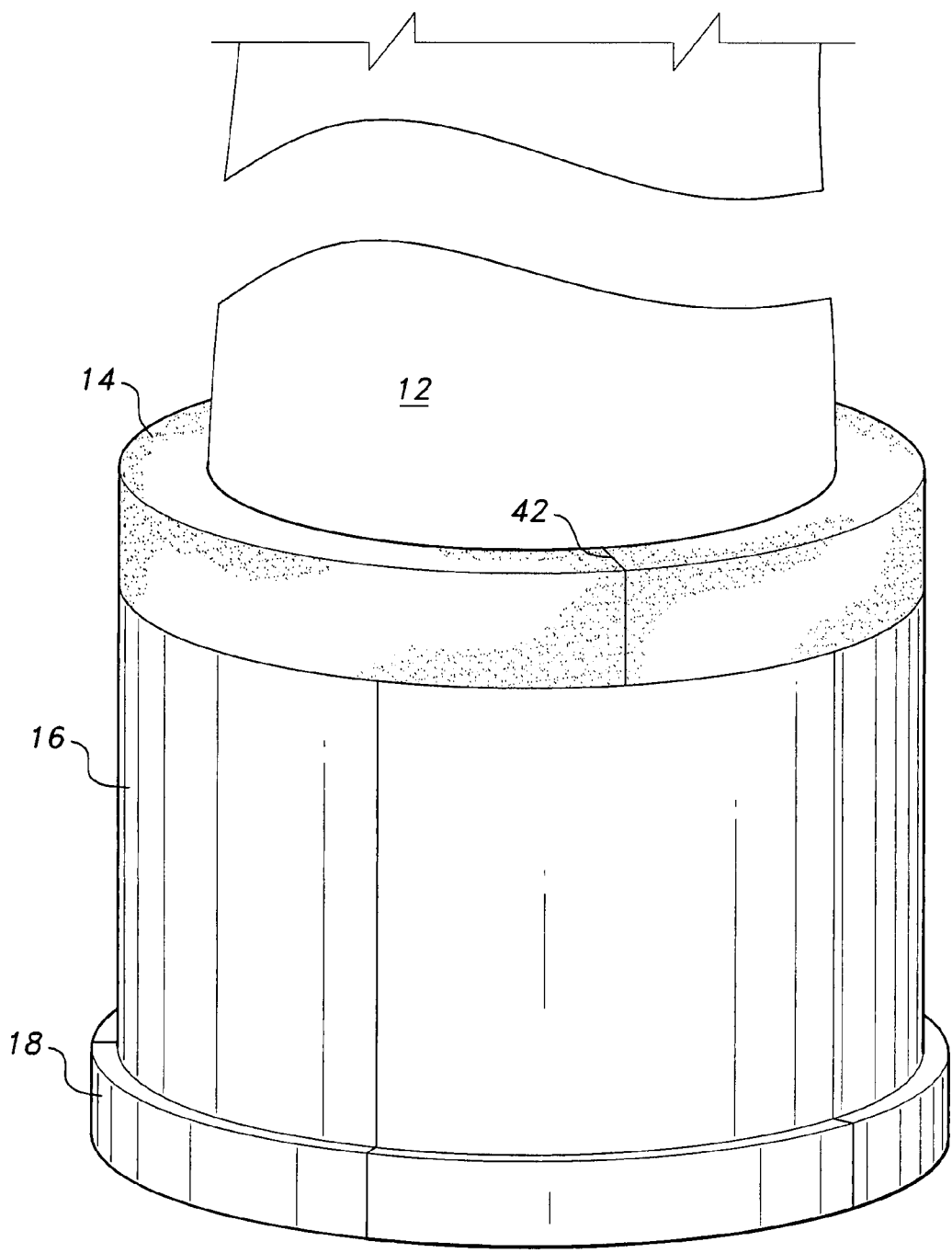
FIG. 5 is a partial environmental, perspective view of the acoustic chamber for detection of insects according to the present invention.

The present invention is directed towards an acoustic chamber for detection of insects. FIG. 1 shows an acoustic chamber 10 placed about an exemplary tree trunk 12. As will be described in greater detail below, chamber 10 is preferably portable and includes a plurality of interlocking elements. During transport and storage, these elements are disassembled and, in use, the system 10 is transported to the location of tree 12 and placed around tree 12 (as shown in FIGS. 1 and 5). Chamber 10 provides a portable enclosure for detecting and analyzing insect life and activity within an insect-infested tree trunk. Although shown as having a substantially cylindrical contour in the drawings, it should be understood that chamber 10 may have any desired shape, e.g., acoustic chamber 10 may be polygonal in transverse section.

As shown in FIGS. 1 and 5, the chamber 10 includes a shell 16 having a segmented annular base 18 and at least one acoustic sensor 20 mounted on shell 16. The acoustic sensor 20 is electrically connected by cable 22 to an interface 24 and a data acquisition system 26, which may be a computer (as illustrated), a programmable logic controller, or any other suitable device for receiving, storing and analyzing acoustic detection signals generated by sensor 20.

Figure 2:
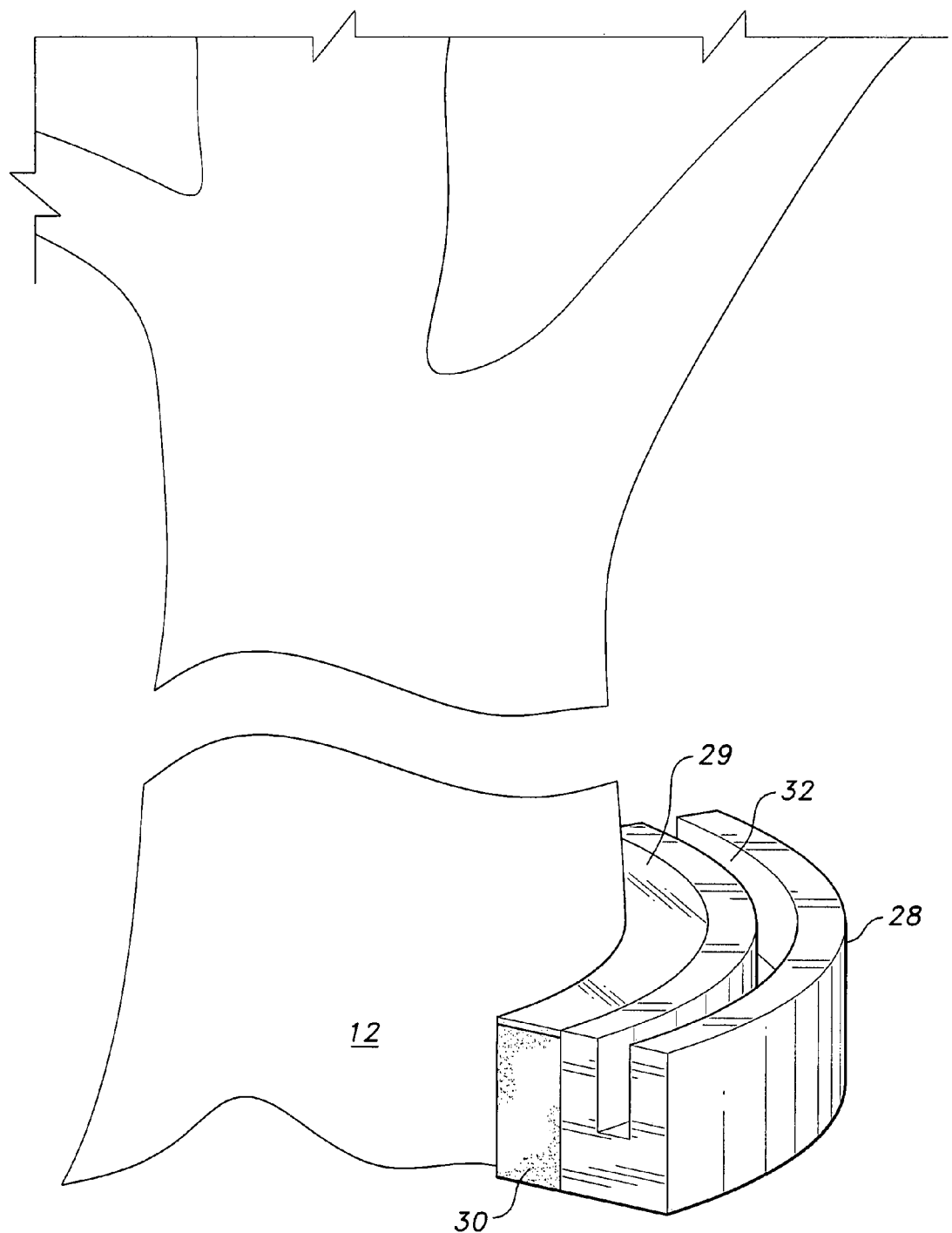
FIG. 2 is an environmental, perspective view of a base member of the acoustic chamber for detection of insects according to the present invention.

Further, as shown in FIG. 2, the upper edge of the annular base preferably has an annular groove 32 formed therein for receiving the lower end of the substantially cylindrical shell 16. FIG. 2 illustrates a single base segment 28, with a plurality of base segments 28 forming annular base 18, as will be described in greater detail below.

Figure 3:
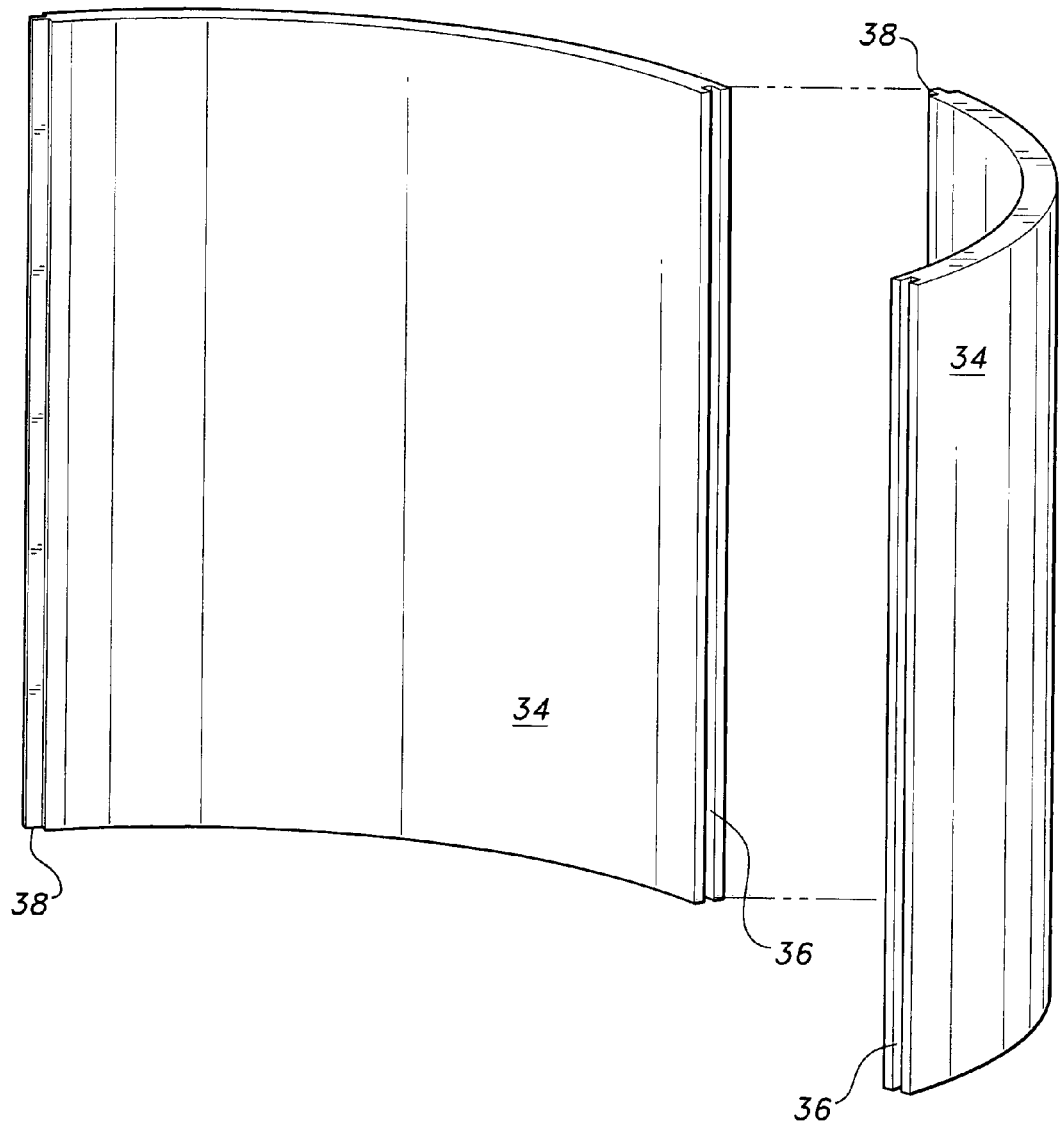
FIG. 3 is a perspective attachment view of a pair of shell members of the acoustic chamber for detection of insects according to the present invention.

A plurality of shell wall members 34 are joined together by tongue-and-groove joints, as best shown in FIG. 3. Each shell member 34 has an elongated groove 36 formed along one edge and an elongated tongue 38 formed along the opposite edge. Adjacent shell wall members 34 are joined by snapping the tongue 38 of one wall member 34 into the groove 32 of the adjoining wall member 34 (or by sliding the tongue 38 into the groove 36).

Similarly, the annular base 18 is preferably formed from a plurality of base segments 28, with the adjacent base segments 28 being held in place by the corresponding shell wall members 34 engaging grooves 32, or by any suitable fasteners, such as tabs, clips, dowels, adhesive, or the like.

Figure 4:
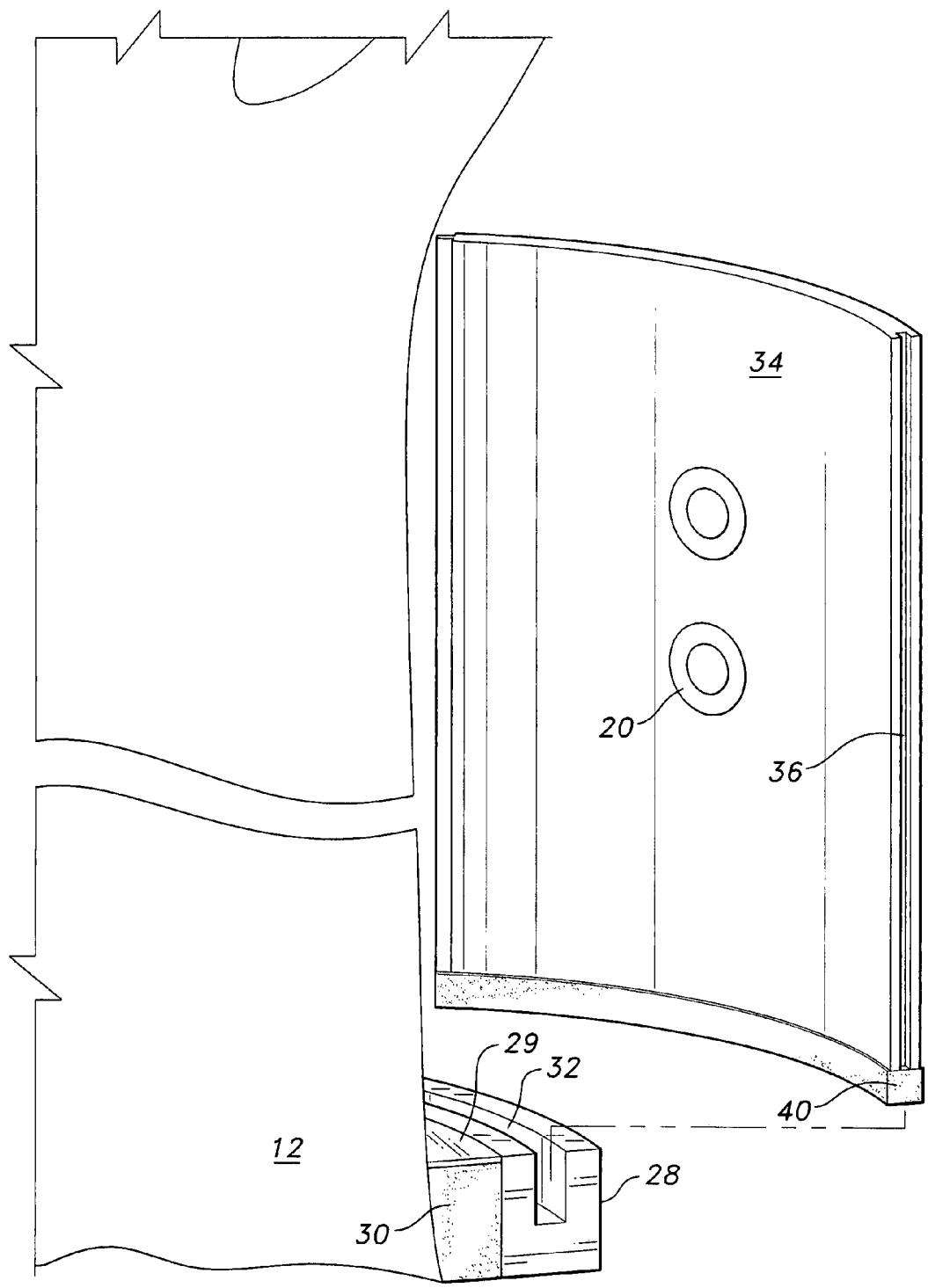
FIG. 4 is a partial environmental, perspective view of the acoustic chamber for detection of insects according to the present invention, showing a shell wall member exploded from the corresponding base member.

As shown in FIG. 4, a gasket 40 or any other suitable seal may additionally be mounted to the lower end of each shell member 34 for enhancing the frictional engagement between the shell member 34 and corresponding base member 28, and for further providing an acoustically insulative seal therebetween.

Figure 6:
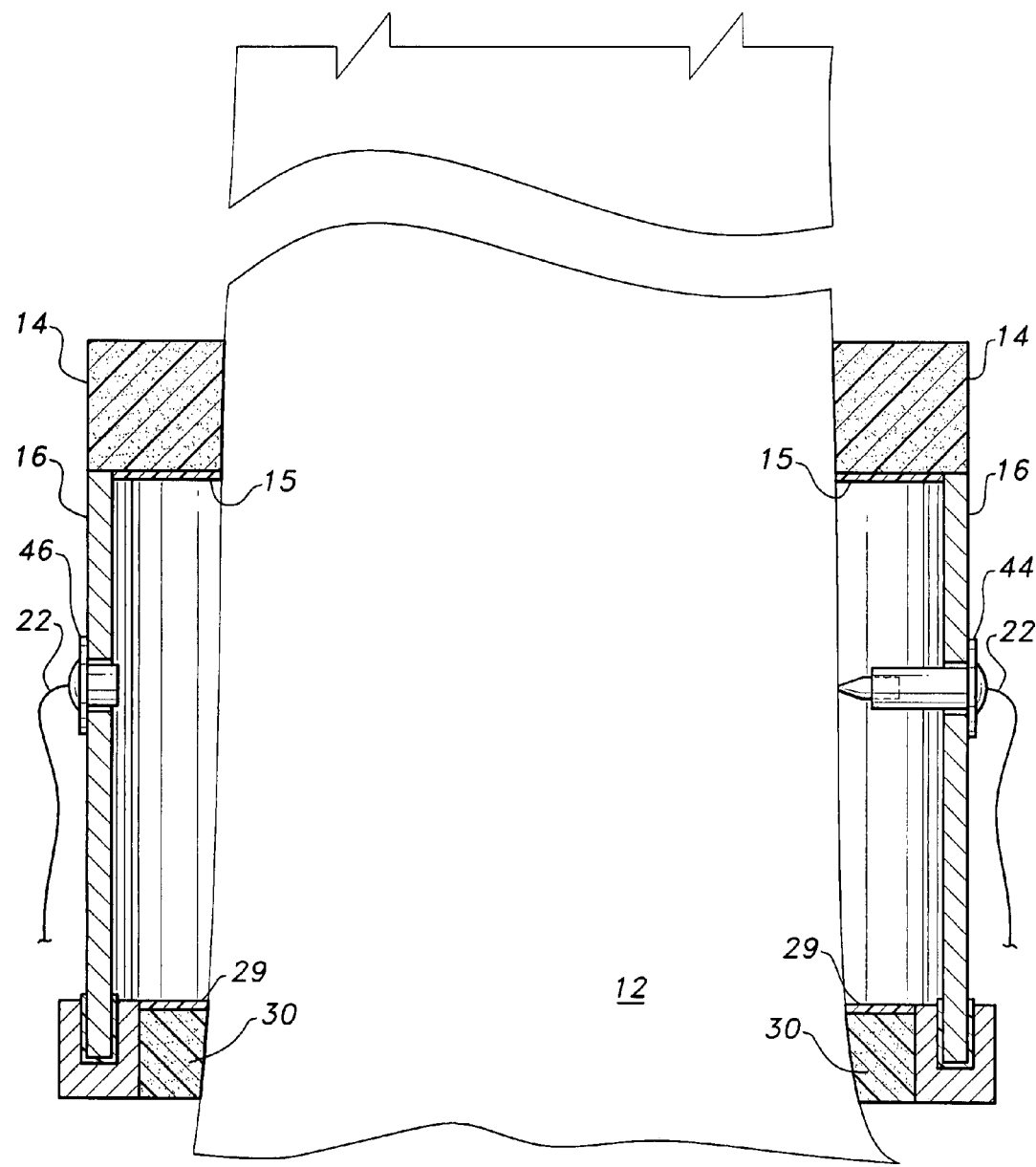
FIG. 6 is an environmental side view in section of the acoustic chamber for detection of insects according to the present invention.

Additionally, an upper annular ring 14 (best shown in FIG. 5) formed from a resilient, spongy, sound-absorbing or sound attenuating material is mounted on the upper end of the shell 16 about the trunk of the tree 12. Ring 14 may be formed in multiple pieces (similar to the multiple shell members 34, for example), or may be formed as a unitary ring with a slit 42 formed therethrough, as illustrated, allowing for positioning of the ring 14 about the tree trunk 12. A lower annular ring 30, similarly formed from a resilient, spongy, sound-absorbing or sound attenuating material, is preferably mounted to an interior surface of the annular base 18 (as shown in FIG. 4), with the lower annular ring 30 being positioned between the tree trunk 12 and the interior surface of the annular base 18. Rings 14, 30 allow the interior of shell 16 and base 18 to be acoustically isolated from the environment. As best shown in FIGS. 2 and 6, a thin layer 29 of acoustically reflective material is preferably formed on the upper surface of ring 30 and a thin layer 15 of acoustically reflective material is formed on the lower surface of ring 14. Thus, sound waves generated by insects within the tree trunk will be reflected by the thin layers 15, 29, forming an acoustic resonance chamber within the shell.

Preferably, the at least one acoustic sensor 20 includes a plurality of acoustic sensors, with at least one of sensors 20 being mounted to each of the shell members 34. The acoustic sensors 20 may be in the form of microphones, acoustic transducers or the like. The acoustic sensors 20 may be in the form of microphones spaced apart from the trunk of the tree (designated generally as 46 in FIG. 6), microphones adapted for contact with the trunk of the tree (designated generally as 44 in FIG. 6), or a combination of the two. Sensors 20 may be receptive to multiple acoustic ranges, dependent upon the nature of insect infestation.

In use, the chamber 10 is transported to the site of the tree 12 with shell members 34 and base members 28 being in a disassembled state. Chamber 10 is placed around tree trunk 12, as shown in FIG. 1, so that microphones 46 and 44 are aligned and positioned to detect insect life within tree trunk 12. Acoustic signals are generated by microphones 46, 44 and are recorded, stored and analyzed within data acquisition or data processing system 26. The acoustic signals represent both a confirmation of insect life and activity within tree trunk 12 and, further, may be analyzed in terms of frequency and intensity to determine the particular nature of insect activity within the trunk; i.e., if the insects are eating, moving, reproducing, etc. Each of these activities produces a unique sonic signature, which may be recorded and analyzed by the user. Interface 24 and/or data acquisition system 26 may further include filters, amplifiers or any other suitable hardware or software selected by the user for the collection and analysis of acoustic data.

It is to be understood that the present invention is not limited to the embodiments described above, but encompasses any and all embodiments within the scope of the following claims.

We claim:

1. An acoustic chamber for the detection of insects, comprising:
   a shell adapted for placement around a trunk of a tree, the shell having a segmented annular base, a plurality of shell wall members supported on the base, and an upper ring disposed on top of the shell wall members, the shell defining an annular acoustic chamber; and
   at least one acoustic sensor mounted on the shell, the sensor being oriented to detect sound within the annular acoustic chamber.

2. The acoustic chamber as recited in claim 1, wherein the plurality of shell wall members are joined together by tongue-and-groove joints.

3. The acoustic chamber as recited in claim 2, wherein said shell wall members are made from a sound-reflecting material.

4. The acoustic chamber as recited in claim 1, wherein each of the plurality of shell wall members has an elongated tongue disposed along one edge and an elongated groove formed along an opposite edge, adjoining shell wall members being joined by connecting the tongues with grooves on the adjoining members.

5. The acoustic chamber as recited in claim 1, wherein said annular base is made from resilient, sound-absorbing material.

6. The acoustic chamber as recited in claim 5, further comprising a layer of sound-reflecting material disposed on said base between the sound-absorbing material and the annular acoustic chamber.

7. The acoustic chamber as recited in claim 1, wherein said upper ring is made from resilient, sound-absorbing material.

8. The acoustic chamber according to claim 7, where said upper ring further comprises a layer of sound-reflecting material disposed between the sound-absorbing material and the annular acoustic chamber.

9. The acoustic chamber according to claim 1, wherein said at least one acoustic sensor comprises a plurality of acoustic sensors.

10. The acoustic chamber as recited in claim 9, wherein the plurality of acoustic sensors comprises at least one audio microphone adapted for being spaced apart from the trunk of the tree.

11. The acoustic chamber as recited in claim 9, wherein the plurality of acoustic sensors comprises at least one contact microphone adapted for contacting the trunk of the tree.

12. The acoustic chamber according to claim 1, further comprising a data processing system electrically connected to said at least one acoustic sensor, the data processing system having means for comparing an audio signal from said acoustic sensor to sound signatures corresponding to activities of pestiferous insects.

13. An acoustic chamber for the detection of insects, comprising:
- a shell adapted for placement around a trunk of a tree, the shell defining an annular sound chamber surrounding the trunk of the tree;
- means for insulating the sound chamber from sound emanating below the shell;
- means for insulating the sound chamber from sound emanating above the shell;
- at least one acoustic sensor mounted on the shell facing the sound chamber, the sensor generating a signal in response to sounds produced by insect activity within the trunk of the tree; and
- a data processing system electrically connected to said at least one acoustic sensor, the data processing system having means for comparing the signal generated by the at least one acoustic sensor to sound signatures corresponding to activities of pestiferous insects in order to detect insect pests within the trunk of the tree.

14. The acoustic chamber according to claim 13, wherein said at least one acoustic sensor comprises a plurality of acoustic sensors.

15. The acoustic chamber according to claim 13, wherein said at least one acoustic sensor comprises a non-contact microphone spaced apart from the tree trunk.

16. The acoustic chamber according to claim 13, wherein said at least one acoustic sensor comprises a contact microphone adapted for positioning in contact with the tree trunk.

17. The acoustic chamber according to claim 13, wherein said means for insulating the sound chamber from sound emanating below the shell comprises a base made from resilient, sound-absorbing material.

18. The acoustic chamber according to claim 17, wherein said base further comprises a layer of sound-reflecting material facing said sound chamber.

19. The acoustic chamber according to claim 13, wherein said means for insulating the sound chamber from sound emanating above the shell comprises an upper ring disposed atop the shell, the upper ring being made from sound-absorbing material.

20. The acoustic chamber according to claim 13, wherein said upper ring further comprises a layer of sound-reflecting material facing said annular sound chamber.

* * * * *